US009765201B2

(12) United States Patent
Mehta et al.

(10) Patent No.: US 9,765,201 B2
(45) Date of Patent: Sep. 19, 2017

(54) COMPOSITION OF MICROWAVABLE PHASE CHANGE MATERIAL

(71) Applicants: Samit Jain, New Delhi (IN); Anil Kumar Mehta, Faridabad (IN); Devendra Jain, New Delhi (IN); Suman Kumari, Guwahati (IN)

(72) Inventors: Anil Kumar Mehta, Faridabad (IN); Devendra Jain, New Delhi (IN); Suman Kumari, Guwahati (IN)

( * ) Notice: Subject to any disclaimer, the term of this patent is extended or adjusted under 35 U.S.C. 154(b) by 0 days.

(21) Appl. No.: 14/438,628

(22) PCT Filed: Oct. 31, 2013

(86) PCT No.: PCT/IB2013/002424
§ 371 (c)(1),
(2) Date: Apr. 26, 2015

(87) PCT Pub. No.: WO2014/064519
PCT Pub. Date: May 1, 2014

(65) Prior Publication Data
US 2015/0274928 A1  Oct. 1, 2015

(30) Foreign Application Priority Data

Oct. 26, 2012  (IN) .......................... 3305/DEL/2012

(51) Int. Cl.
*C08K 3/04* (2006.01)
*C08K 3/34* (2006.01)
*C08K 5/09* (2006.01)
*A47J 36/02* (2006.01)
*A61F 7/02* (2006.01)

(52) U.S. Cl.
CPC .............. *C08K 5/09* (2013.01); *A47J 36/027* (2013.01); *A61F 7/02* (2013.01); *C08K 3/04* (2013.01);
(Continued)

(58) Field of Classification Search
CPC ........... C08K 3/04; C08K 3/346; C08K 3/043
(Continued)

(56) References Cited

U.S. PATENT DOCUMENTS 4,190,757 A * 2/1980 Turpin ............... B65D 81/3446
219/729
4,982,064 A * 1/1991 Hartman ............ B65D 81/3469
219/727

(Continued)

OTHER PUBLICATIONS

Kashimura et al, Surface-plasmon-like modes of graphite powder compact in microwave heating, J. of Appl. Phys. 112, 034905 (2012).*

(Continued)

*Primary Examiner* — Holly Le
(74) *Attorney, Agent, or Firm* — Helix Patent Services LLC

(57) ABSTRACT

The present invention provides a microwavable Phase Change Material and product thereof, particularly, the present invention relates to the field of microwave heating and use of microwave susceptor for providing heat to Phase Change Material. The invention provides a new process for preparing improved Phase Change Material which can be heated in a domestic microwave oven. The inventive composition comprises of a microwave susceptor which helps the Phase Change Material to melt within a few minutes depending upon the quantity of Phase Change Material taken. Microwave susceptor is at first uniformly mixed with some other material. The other material may be a highly conductive material, or a slow susceptor. Then this composite is incorporated in a Phase Change Material. This susceptor composite initiates uniform melting of Phase Change Material when exposed to microwave irradiation. This microwavable Phase Change Material is free of sparking, arcing and local overheating.

11 Claims, 3 Drawing Sheets

(52) U.S. Cl.
CPC .............. *C08K 3/042* (2017.05); *C08K 3/346* (2013.01); *A61F 2007/0204* (2013.01); *A61F 2007/0214* (2013.01); *A61F 2007/0242* (2013.01); *A61F 2007/0292* (2013.01); *Y10T 428/2982* (2015.01)

(58) Field of Classification Search
USPC .............................. 428/402, 688; 252/182.32
See application file for complete search history.

(56) References Cited

U.S. PATENT DOCUMENTS

| | | | | |
|---|---|---|---|---|
| 5,132,144 | A * | 7/1992 | Parks ...................... | B41M 3/00 101/491 |
| 5,343,024 | A * | 8/1994 | Prosise .............. | B65D 81/3453 219/730 |
| 5,565,132 | A | 10/1996 | Salyer | |
| 5,804,266 | A | 9/1998 | Salyer | |
| 2009/0035562 | A1* | 2/2009 | Fukushima ............... | C22C 1/10 428/337 |
| 2012/0048768 | A1* | 3/2012 | Holloway .............. | C09K 5/063 206/524.1 |

OTHER PUBLICATIONS

Sari, Ahmet: "Form-stable paraffin/high density polyethylene composites as solid-liquid phase change material for thermal energy storage: preparation and thermal properties", Energy Conversion and Management, vol. 45, Issues 13-14, Aug. 2004, pp. 2033-2042.

* cited by examiner

COMPOSITION OF MICROWAVABLE PHASE CHANGE MATERIAL

FIELD OF THE INVENTION

The present invention relates to a microwavable Phase Change Material (PCM) and products thereof. Particularly, the present invention relates to the field of microwave heating, use of microwave susceptor for providing heat to Phase Change Material (PCM) and a new composition of a microwavable Phase Change Material (PCM).

BACKGROUND

Phase Change Material (PCM) is suitable for storing thermal energy in the form of latent heat. Microwave energy is changed to heat as soon as it is absorbed by a microwave susceptor.

Every microwave oven contains a magnetron, a tube in which electrons are affected by magnetic and electric field in such a way as to produce micro wavelength radiation at about 2.45 GHz. In commercial microwave oven, the oven has a power input of about 1000 watts of alternating current. As these microwaves generated from magnetron bombard the PCM, they cause the polar molecules to rotate at the same frequency millions of times a second. This agitation creates molecular friction, which heats up the PCM.

U.S. Pat. No. 5,070,223 discloses an article of apparel in which microwave sensitive material is present in only one portion. The overheating generated at this portion heats the whole article.

U.S. patent application Ser. No. 11/511,775 describes the use of carbon black as conductive particulate material in nano scale. Our invention does not require carbon black in such a minute particle size.

U.S. Pat. No. 5,310,977 demonstrates a metalized film susceptor with aluminum metal layer patterned to form a film which produces too much heat locally.

U.S. Pat. No. 5,630,961 discloses a microwavable thermal storage composition which is free flowing powder. However this patent does not tell about cycling stability of Phase Change Material (PCM). It also does not tell whether it remains in free flowing powder form after one melting and freezing cycle or not.

U.S. Pat. No. 4,962,000 discloses a composite with two microwave absorbing zones which are being separated by a microwave transparent layer with a pressure sensitive adhesive. This also discloses that composite is incapable of arcing but doesn't mention anything about overheating.

Further, other prior art approaches are also subject to many variations. For example, U.S. patent application Ser. No. 11/906,730 discloses a phase transition golf ball in which a portion of golf ball comprising microwave susceptor is heated more rapidly to a higher temperature in comparison with a portion of golf ball that does not contain microwave susceptor. This shows that susceptor is accumulated at one point to heat the whole article.

In normal microwavable Phase Change Material (PCM), people face many problems after using it for a number of times. After some melting cycles the microwave susceptor becomes inactive. Thus the Phase Change Material (PCM) takes more time to charge or does not charge at all. Heat generated by microwave gets concentrated at a few points and then this concentrated heat is used to melt the whole Phase Change Material (PCM). Due to this degradation of Phase Change Material (PCM) occurs and essentially from these points heat is transmitted by convection only, thus leading to spots of very high temperature or non-uniformity of temperature all over the surface. Also due to use of high percentage of microwave susceptor, latent heat value of microwavable Phase Change Material (PCM) decreases.

Microwavable hot or cold packs which are commercially available are water based and in liquid phase. Phase transition does not occur after microwave heating. It remains in only liquid state. Thus only sensible heat is used for heating application which is 2-3 times less than Phase Change Material (PCM).

Therefore there exists a need for a microwave sensitive Phase Change Material (PCM) which is more effective and efficient.

The novelty in the present invention resides in providing a new form of microwave susceptor incorporating a Phase Change Material (PCM) and a binding agent like clay. This new composition prevents the agglomeration of the susceptor. Also there will be uniform heating (charging) and discharging—again because of no agglomeration or sedimentation of susceptor, thus no Phase Change Material (PCM) degradation. Uniform distribution of susceptor means lower amount can be used. Thus latent heat of resultant Phase Change Material (PCM) composition is high according to the present invention. No change in workability/efficiency of Phase Change Material (PCM) occurs, even after several charging and discharging cycles. Phase Change Material (PCM) takes only 2-3 minutes time depending on quantity for melting/charging in 1000 watt domestic microwave. For example if we take 100 grams of microwavable Phase Change Material (PCM), on exposing to microwave irradiation in domestic microwave oven ing, it melts in just 30 sec to 60 sec time duration.

SUMMARY

It is an object of the present invention to provide a microwavable Phase Change Material (PCM) and product thereof, particularly relates to the field of microwave heating and use of microwave susceptor for providing heat to Phase Change Material (PCM).

Another object of the present invention is to provide a process for preparing microwavable Phase Change Material (PCM) and product.

Another object of the present invention is to provide a microwavable Phase Change Material (PCM) and product, wherein it prevents agglomeration of the susceptor.

Another object of the present invention is to provide a microwavable Phase Change Material (PCM) and product, wherein there will be uniform heating and discharging because of no agglomeration or sedimentation of susceptor, thus no Phase Change Material (PCM) degradation.

Yet another object of the present invention is to provide a microwavable Phase Change Material (PCM) and product, wherein uniform distribution of susceptor means lower amount can be used. Thus latent heat of resultant Phase Change Material (PCM) is high.

Yet another object of the present invention is to provide a microwavable Phase Change Material (PCM) and product, wherein no change in workability/efficiency of PCM occurs, even after several charging and discharging cycles.

Yet another object of the present invention is to provide a microwavable Phase Change Material (PCM) and product, wherein Phase Change Material (PCM) takes only 2-3 minutes time for melting/charging in a 1000 watt domestic microwave.

Yet another object of the present invention is to provide a microwavable Phase Change Material (PCM) and product, wherein microwavable Phase Change Material (PCM) does not generate any spark or arc or local overheating.

Thus the present invention provides a microwavable Phase Change Material (PCM) and product thereof, particularly relates to the field of microwave heating and use of microwave susceptor for providing heat to Phase Change Material (PCM). The susceptor is a substance for converting microwave energy to heat, that in turn heats another substance. Microwave susceptor is at first uniformly mixed with some binding agent. Then this composite is incorporated in a Phase Change Material (PCM). This susceptor composite initiates uniform melting of Phase Change Material (PCM) when exposed to microwave irradiation. This microwavable Phase Change Material (PCM) is free of sparking, arcing and local overheating.

Further, the microwavable Phase Change Material (PCM) comprises 30% to 99.9% by weight of a Phase Change Material (PCM) or mixture of a Phase Change Material (PCM) and polymer, and 0.1% to 70% by weight of a composite material comprising a microwave susceptor and a binding agent.

In an embodiment, clay is used as a binding agent and a slow susceptor in the composite.

BRIEF DESCRIPTION OF THE FIGURES

The features of the present invention, which are believed to be novel, are set forth with particularity in the appended claims. The invention may best be understood by reference to the following description, taken in conjunction with the accompanying figures. These figures and the associated description are provided to illustrate some embodiments of the invention, and not to limit the scope of the invention

DETAILED DESCRIPTION OF THE INVENTION

Figure 1:
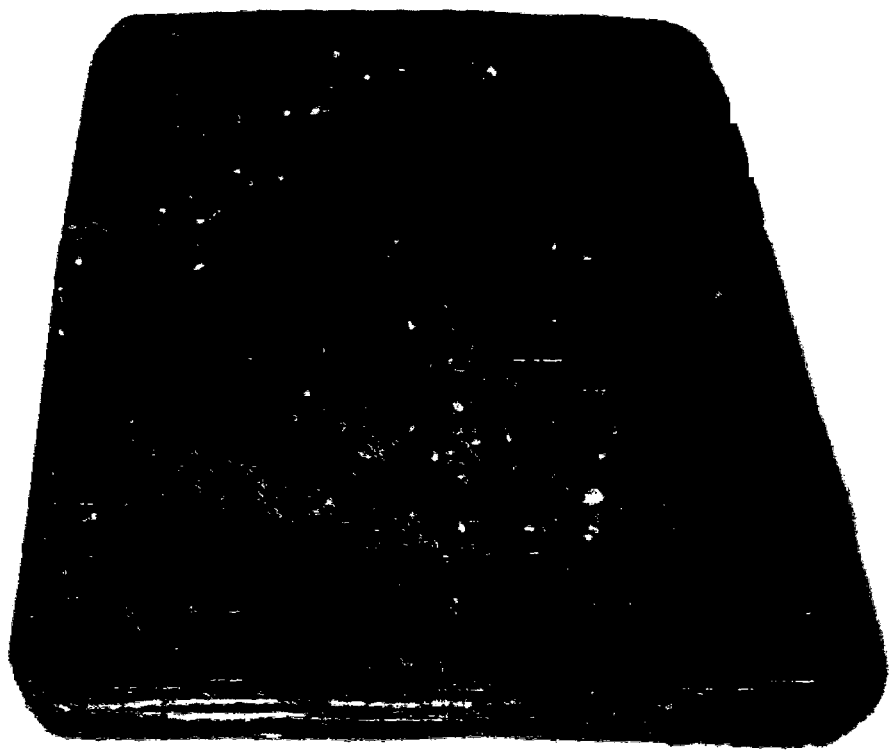
FIG. 1 shows a microwavable Phase Change Material (PCM) in solid state.

Before describing the invention in detail, it should be observed that while the specification concludes with the claims defining the features of the invention that are regarded as novel, it is believed that the invention will be better understood from a consideration of the following description in conjunction with the figures, in which like reference numerals are carried forward.

As required, detailed embodiments of the present invention are disclosed herein; however, it is to be understood that the disclosed embodiments are merely exemplary of the invention, which can be embodied in various forms. Therefore, specific functional and compositional details disclosed herein are not to be interpreted as limiting, but merely as a basis for the claims and as a representative basis for teaching one skilled in the art to variously employ the present invention in virtually any domain. Further, the terms and phrases used herein are not intended to be limiting but rather to provide an understandable description of the invention.

The terms "a" or "an", as used herein, are defined as one or more than one. The term "another", as used herein, is defined as at least a second or more. The terms "including" and/or "having" as used herein, are defined as comprising (i.e. open transition).

The foregoing objects of the present invention are accomplished and the problems and shortcomings associated with the prior art, techniques and approaches are overcome by the present invention, as described below in the preferred embodiments.

The present invention discloses a microwavable Phase Change Material (PCM) comprising a composite material formed from a microwave susceptor and a binding agent. The microwavable Phase Change Material (PCM) further comprises a Phase Change Material or a mixture of a polymer and a Phase Change Material.

The composite material comprises 0.1% to 70% of the weight of the microwavable Phase Change Material (PCM). Clay is used as a binding agent in the composite material. The material for the microwave susceptor is selected from the group consisting of metals, semiconductors, non-metals or their mixture; preferably graphite or carbon black and has a particle size between 20 nm to 1 min. In certain embodiments the microwave susceptor has a particle size ranging from 10 microns to 100 microns. The composite material imparts microwave heating capability and thermal conductivity to the Phase Change Material. Moreover the clay in the composite prevents the agglomeration and provides shear during uniform mixing with Phase Change Material.

The Phase Change Material (PCM) is selected from the group comprising organic chemicals, inorganic chemicals, eutectic chemicals preferably organic, and eutectic chemicals and their mixture. The Phase Change Material (PCM) comprises 30% to 99.9% of the weight of the microwavable Phase Change Material (PCM). In an embodiment a mixture of polymer and Phase Change Material (PCM) is used.

The microwavable Phase Change Material (PCM) further comprises a thermally conductive material which provides uniform heating, and uniform discharging of the said material. Moreover the thermally conductive material removes arcing, sparking and overheating during microwaving. Also the microwavable Phase Change Material (PCM) has a high latent heat storage capacity.

This microwavable Phase Change Material (PCM) can be molded and cast into pellet form, cubical form, spherical form, sheet form and various other shapes and sizes. For example the microwavable Phase Change Material (PCM) can be used in table ware items, hot plates, food warmers medical wraps, and any heating application material.

The present invention discloses a process for preparing improved Phase Change Material (PCM) which can be heated in a domestic microwave oven. The microwave susceptor, preferably carbon black, is at first combined with inert clays, binding agent or other similar material. 10% to 90% by weight of carbon black is added to inert clay composite. Inert clay has high temperature resistance. This composite is mixed uniformly with the use of water and/or adhesive, glue or such material. It is then left over for drying. On drying it becomes hard and tough. Uniformity of carbon black can be seen in this microwave susceptor composite. On processing, the dried carbon inert clay composite can be converted into granular form. This composite prevents carbon particles from agglomeration when placed in a microwave oven. These shapes may be spherical or any other irregular shape. This compounded microwave susceptor does not agglomerate on mixing & microwave heating of Phase Change Material (PCM).

In an embodiment of the present invention, the microwave susceptor has a particle size of about 20 nm to 1 mm.

In another embodiment of the present invention, the microwave susceptor can be carbon black or other microwave sensitive material such as metallized plastic film, ceramics, aluminum flakes, silicon carbide, aluminum metallized polyester (PET) sheet, glycerine, rubber latex, carbon, graphite, polyurethane with fine powder of carbon, graphite, water molecule, suitable hydrated crystals of aluminum nitrate, calcium acetate, calcium chloride, calcium nitrate, chromium nitrate, copper nitrate, iron chloride, magnesium chlorate, potassium fluoride, potassium phosphate, sodium acetate, sodium carbonate, sodium chlorite, sodium phosphate, sodium chromate, ferrite, soft ferrite, ferrite alloys including nickel ferrite and magnesium ferrite, magnetite, lithium ferrite, carbonyl iron, iron steel, iron oxide, ferric oxide, carbons including amorphous carbon, graphite in the form of particles, fibers or filaments, carbon chunks, charcoal, activated charcoal, carbon fibers, carbon filaments, carbon black, lamp black, furnace black and channel black, polyesters including alpha-beta unsaturated polyesters, aluminum including small particles or flakes thereof, gadolinium trichloride, boron trichloride, boron, barium titanate, strontium titanate, lead titanate, lead niobate, lead zicornate, nickel oxide, zinc oxide, silicon carbide, polyacetylene, cobalt, nickel, polycrystalline yttrium iron garnate, yttrium barium copper oxide, tin oxide, titanium dioxide, germanium dioxide, semiconductor, butter fat and microwave transducing lipids including those with unsaturated bonds and mixture thereof. The person skilled in the art will know that not all susceptors can be used with all Phase Change Materials (PCM). The susceptor and Phase Change Material (PCM) have to be compatible and non-reactive.

In conventional Phase Change Materials (PCM), it is found that simply addition of susceptor in Phase Change Material (PCM) does not keep it suspended in Phase Change Material (PCM). On microwaving, it gets accumulated, deposits at the bottom or floats at the surface of Phase Change Material (PCM) due to density difference, causing non-uniform heating in Phase Change Material (PCM).

This problem can be reasonably reduced or eliminated by addition of susceptor-clay in Phase Change Material (PCM) susceptor mixture. Clay susceptor mixture can be added for better suspension of susceptor in Phase Change Material (PCM) matrix.

Addition of clay in microwavable Phase Change Material (PCM) has the following advantages:
(i) Clay is slow microwave susceptor. It generates heat during Phase Change Material (PCM) microwaving and thus reduces the microwaving time of the Phase Change Material (PCM).
(ii) It provides shear on mixing during manufacturing process.
(iii) It substantially reduces the exudation from Phase Change Material (PCM) composite.

Although additives add extra properties to Phase Change Material (PCM), they also compromise with the latent heat of the Phase Change Material (PCM).

In one embodiment of the present invention, one or more types of clay are selected from the group comprising of china clay, fired brick clay, bentonite clay, organo clay, fuller's earth, montmorillonite clay and attapulgite clay. Here the fired brick clay powder includes byproduct of brick kiln or other sintered or fired clay products.

In another embodiment of the present invention, this susceptor-clay composite is dispersed uniformly in a Phase Change Material (PCM). In a particular embodiment 0.1%-70% by weight of microwave susceptor and clay are added to the Phase Change Material (PCM). This addition of microwave susceptor and clay, imparts microwave heating capability and thermal conductivity to the Phase Change Material (PCM). Incorporation of this susceptor clay composite can be done in two ways:—

In one embodiment, this composite microwave susceptor is uniformly mixed with a Phase Change Material (PCM) or a Form Stable Phase Change Material (FSPCM), and added or suspended during preparation of the Form Stable Phase Change Material (FSPCM). Thus Form Stable Phase Change Material (FSPCM) becomes a microwavable Form Stable Phase Change Material (FSPCM).

In another embodiment, a method of using the compounded microwave susceptor in the present invention includes the use of screens made of plastic or textile fiber/fabric that are inert to Phase Change Material (PCM). One example of fabric is polyester in the form of a grid.

The final product thus obtained by the addition on susceptor-clay composite to the PCM consists of 30%-99.9% by weight of the Phase Change Material (PCM).

In another embodiment of the present invention about 0.1%-70% of carbon black-clay composite is used as microwave susceptor in Phase Change Material (PCM).

The addition of susceptor composite initiates uniform melting of Phase Change Material (PCM) when exposed to microwave irradiation. The absorption of microwaves by a material results in the microwaves giving up their energy to the material. This transfer of energy causes the temperature of the material to rise. Also the microwavable phase change material has high thermal conductivity, which initiates uniform melting even when Phase Change Material (PCM) is exposed to non-uniform microwave irradiation.

In another embodiment of the present invention, the susceptor composite granules can also be dispersed in clay/porous material or foam or fibers or fabrics or Phase Change Material (PCM) such that it could not agglomerate. This process also makes the entire composite, in which susceptor composite is incorporated, as microwavable.

In another embodiment of the present invention, the invention is useful for applications such as jackets for heating applications, article of apparel, food warmer, hot wrap, medical wrap and various other heating applications.

In another embodiment of the present invention Phase Change Material (PCM) used for preparing microwavable thermal storage material include paraffin, organic substance, inorganic substance, fatty acid, wax and eutectic mixture.

The technological challenge of the present invention is not just to expose the Phase Change Material (PCM) to a higher temperature, but to control the temperature so that the Phase Change Material (PCM) will uniformly melt without charring, arcing and overheating. The present invention shows a great potential in all these areas.

Optimum microwaving time in a specific microwave oven depends on the following:
(i) quantity of microwavable Phase Change Material (PCM) taken,
(ii) proportion of susceptor present in the Phase Change Material (PCM),
(iii) ability of susceptor to convert microwave radiation to heat energy
(iv) latent heat of Phase Change Material (PCM) taken.

Thermal conductivity is the property of a material's ability to conduct heat. Every microwave oven contains a magnetron, a tube in which electrons are affected by magnetic and electric field in such a way as to produce micro wavelength radiation at about 2.45 GHz. As these microwaves generated from magnetron bombard the Phase Change Material (PCM), they cause the polar molecules to rotate at the same frequency. As this agitation of the polar molecules creates molecular friction, the Phase Change Material (PCM) gets heated up.

The concentration of microwave radiation does not remain even inside the oven while it runs. The rotating glass tray on which food or microwavable Phase Change Material is placed helps to uniformly heat up the material. But the rotating glass tray does not help in uniform distribution of microwave radiation in radial direction. Thus the microwavable Phase Change Material (PCM) no longer heats up uniformly. To remove this problem, a high thermal conductivity material needs to be incorporated in the Phase Change Material (PCM). Thermal conductivity of Phase Change Material (PCM) can be improved greatly by adding a thermally conductive material.

With the thermally conductive materials, the heat instantly gets transmitted to adjacent Phase Change Material particles. Moreover the thermal conductive material removes sparking or over heating during microwaving and provides uniform heating and uniform discharging of the said material.

Figure 3:
FIG. 3 [Prior Art] shows a, microwaved. Phase Change Material (PCM) with patches of hot spots, wherein mid portions remain solid even after 1 minute of microwaving in 800 W oven.

Poor thermal conductivity of Phase Change Material limits effective charging in microwave oven. In poor conductive microwavable. Phase Change Material (PCM) only outer edges get heated up, and in some only mid portion get heated up. Due to this, sparking or hot spot occurs and rest of the portion remains solid, as can be seen in FIG. 3. If Phase Change Material (PCM) is left inside microwave oven for longer duration, then it gets damaged or degraded.

In another embodiment of the present invention, one or more thermal conductive materials may be selected from the group comprising of graphite powder, graphene, metallic oxide powder, aluminum, brass, cadmium, carbon graphite, carbon fibers, copper, gold, diamond, iron, nickel, platinum, quartz, silver, tin, some conductive polymers such as melamine, polyanilines, polypyrrols, polythiophenes, carbon fibers or any other conductive materials which are available in prior art.

The material may be a good microwavable susceptor as well as good heat conductor. Any additives add extra properties to microwavable Phase Change Material (PCM) but also compromise with the latent heat of Phase Change Material.

Non uniform heating or hot spot forming in microwavable Phase Change Material (PCM) is prevented by better methods of mixing susceptor in the Phase Change Material (PCM) matrix and by adding high thermal conductivity material.

Example 1

100 g of stearic acid was taken in a glass beaker. 0.3 g of carbon black was uniformly mixed in stearic acid with a spatula. It was then microwaved. The whole mixture melted in 2 min of microwaving in 800 W oven. It was then kept aside for solidification at room temperature. On solidification it was noticed that carbon black settles at the bottom of glass beaker. Again on microwaving, heat was generated only at the bottom and above that heat generation was unnoticed. This showed uneven heating. Thus it is concluded that carbon black sediments at the bottom of container leads to high concentration of heat at that point.

Example 2

80 g of SavE Reinforced. Form Stable 65 Phase Change Material (RFS65PCM) from Pluss Polymers Pvt. Ltd. and 80 g of fired brick clay powder as susceptor was mixed at 110° C. and casted in the form of circular sheet of weight 160 g. On microwaving only edges got heated up and on further microwaving the edges melted but the centre portion remained solid. This was due to very low thermal conductivity of fired clay particles. Heat generated from microwaving could not transfer to the adjacent portion. Thus it is inferred that high thermal conductivity material is required in microwavable PCM sheet.

Example 3

Figure 2:
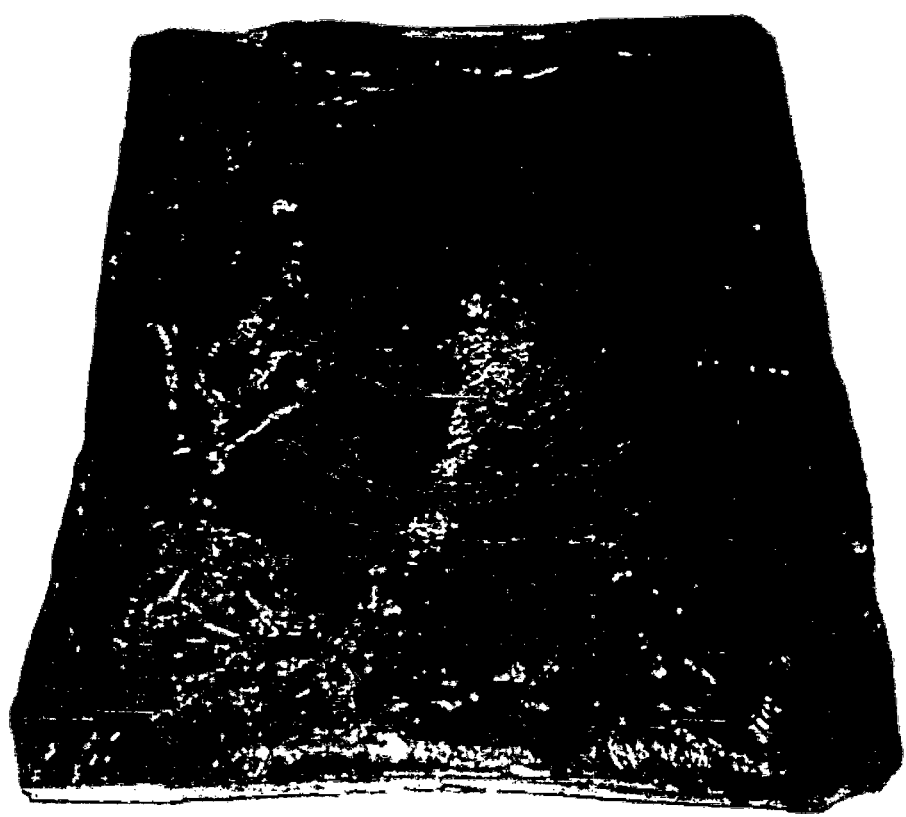
FIG. 2 shows a microwaved and uniformly heated microwavable Phase Change Material (PCM) and illustrates a thermally conductive Phase Change Material (PCM)

A procedure of preparing microwavable Phase Change Material (PCM) is illustrated here. 150 grams of Reinforced Form Stable 65 Phase Change Material (RFS65PCM) at 110° C. was taken in a stainless steel container. In this 7.5 g of expanded graphite powder was added and mixed with a stirrer. The mixture was cast in the form of a rectangular sheet. It was then cooled at room temperature for solidification as demonstrated in FIG. 1. Thus a microwavable PCM sheet was obtained. On microwaving the sheet for 3 minutes in an 800 W domestic oven, uniform heating was observed because of increased thermal conductivity. There were no hot spots or patches, which is also shown in FIG. 2.

Example 4

A process of preparing microwavable Phase Change Material (PCM) is described in this example. 142 grams of savE Reinforced Form Stable 65 Phase Change Material (RFS65PCM) from Pluss Polymers was taken. Then it was heated to a temperature of 120° C. in a stainless steel container. In a separate container graphite and clay powder in the ratio of 1:6 respectively was mixed. 58 g of graphite-clay mixture was added in RFS 65 PCM and constantly stirred at 120° C. temperature to get a uniform blend. The blend was cast in the form of rectangular sheet. It was then cooled at room temperature for solidification as shown in FIG. 1. Thus a microwavable Phase Change Material (PCM) sheet was obtained.

Example 5

This test was done to check the optimum microwaving time for 430 g of microwavable Phase Change Material (PCM) sheet. The microwavable Phase Change Material (PCM) sheets were prepared by the same method as explained in example 4. Two FSM 65 sheet of combined weight of 430 g were heated in 800 W domestic microwave oven. Then these micro waved sheets were put inside an empty lunch bag. Temperature data logger was placed between the two sheets and the lunch bag zip was closed. Since the Phase Change Material (PCM) is of phase change, temperature of 65° C. so back up time for FSM Phase Change Material (PCM) sheet was considered only from temperature 69° C. to 63° C. This was repeated eight times with different microwaving time run and the data is listed in table below:

| SI no. | FSM65 Microwaving time in 800 w domestic oven | Back up time (from 69° C. to 63° C.) |
| --- | --- | --- |
| 1. | 30 sec | 0 |
| 2. | 1 min | 0 |
| 3. | 1 min 30 sec | 30 min |
| 4. | 2 min | 43 min |

| SI no. | FSM65 Microwaving time in 800 w domestic oven | Back up time (from 69° C. to 63° C.) |
|---|---|---|
| 5. | 2 min 30 sec | 1 hr 20 min |
| 6. | 3 min | 1 hr 42 min |
| 7. | 3 min 30 sec | 2 hr 2 min |
| 8. | 4 min | 2 hr 3 min |

The above test indicates the optimum microwaving time for 430 g of savE FSM 65 PCM slab in 800 w domestic microwave oven is 3 min 30 sec. Optimum microwaving time depends on quantity of microwavable Phase Change Material (PCM) taken.

In an embodiment the microwavable Phase Change Material (PCM) obtained as such, can be moulded cast into various shape and sizes such as sheet form of minimum thickness of 0.1 mm, pellets form, cubical form, spherical shape or any other according to desired application.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

We claim:

1. A microwavable Phase Change Material (PCM) comprising:
   i. 30% to 84% by weight of a Phase Change Material (PCM) or a mixture of a Phase Change Material and a polymer; and
   ii. 16% to 70% by weight of a composite material comprising a microwave susceptor and a binding agent, the composite material comprising graphite as a primary microwave susceptor and clay as a secondary microwave susceptor, wherein graphite also acts as a thermal conductivity enhancer and clay additionally acts as a binding agent and a dispersant.

2. The microwavable Phase Change Material (PCM) according to claim 1, wherein the Phase Change Material (PCM) is selected from the group comprising organic chemicals, inorganic chemicals, organic eutectic chemicals, and eutectic chemicals and mixture thereof.

3. The microwavable Phase Change Material (PCM) according to claim 1, wherein the clay provides shear during mixing with the Phase Change Material.

4. The microwavable Phase Change Material (PCM) according to claim 1, wherein the composite material imparts microwave heating capability and thermal conductivity to the Phase Change Material (PCM).

5. The microwavable Phase Change Material (PCM) according to claim 1, wherein the microwave susceptor also comprises metals, semiconductors, non-metals or their mixture and carbon black.

6. The microwavable Phase Change Material (PCM) according to claim 1 further comprising a thermally conductive material, wherein the thermal conductive material removes arcing, sparking, and overheating during microwaving and provides uniform heating, and uniform discharging of the said material.

7. The microwavable Phase Change Material (PCM) according to claim 1, wherein the microwavable Phase Change material is used in table ware items, hot plate, food warmer, medical wrap, and other heating application based items.

8. The microwavable Phase Change Material (PCM) according to claim 1, wherein the microwavable Phase Change material is molded and cast into various shape and sizes, pellet form, cubical form, spherical form, and sheet form.

9. The microwavable Phase Change Material (PCM) according to claim 1, wherein the primary microwave susceptor has a particle size ranging between 20 nm to 1 mm.

10. The microwavable Phase Change Material (PCM) according to claim 1, wherein the Graphite has a particle size ranging between 10 to 100 microns.

11. The microwavable Phase Change Material (PCM) of claim 1, wherein the clay reduces the exudation from Phase Change Material (PCM) composite.

* * * * *